US010426401B2

(12) United States Patent
Bokan et al.

(10) Patent No.: US 10,426,401 B2
(45) Date of Patent: Oct. 1, 2019

(54) SIGNAL CHARACTERIZATION TO FACILITATE THERAPY DELIVERY (71) Applicant: CARDIOINSIGHT TECHNOLOGIES, INC., Independence, OH (US)

(72) Inventors: Ryan Bokan, Cleveland, OH (US); Charulatha Ramanathan, Solon, OH (US); Ping Jia, Solon, OH (US); Meredith E. Stone, Strongsville, OH (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 644 days.

(21) Appl. No.: 14/839,299

(22) Filed: Aug. 28, 2015

(65) Prior Publication Data

US 2016/0058369 A1 Mar. 3, 2016

Related U.S. Application Data

(60) Provisional application No. 62/043,786, filed on Aug. 29, 2014.

(51) Int. Cl.
*A61B 5/00* (2006.01)
*A61B 5/044* (2006.01)
(Continued)

(52) U.S. Cl.
CPC ............ *A61B 5/4836* (2013.01); *A61B 5/743* (2013.01); *A61B 5/7425* (2013.01); *A61B 5/044* (2013.01); *A61B 5/04012* (2013.01); *G16H 40/63* (2018.01)

(58) Field of Classification Search
CPC ..... A61B 5/4836; A61B 5/743; A61B 5/7425; A61B 5/04012; A61B 5/044; G16H 40/63
See application file for complete search history.

(56) References Cited

U.S. PATENT DOCUMENTS 5,020,540 A 6/1991 Chamoun
5,348,020 A 9/1994 Hutson
(Continued)

FOREIGN PATENT DOCUMENTS

CN 103153390 A 6/2013
EP 3102102 A1 12/2016

OTHER PUBLICATIONS

European Application No. 15837052.8, filed Aug. 28, 2015; Supplementary European Search Report; Date of Completion: Mar. 23, 2018; 8 pgs.

(Continued)

*Primary Examiner* — Joseph M Santos Rodriguez
(74) *Attorney, Agent, or Firm* — Tarolli, Sundheim, Covell & Tummino (57) ABSTRACT

An example method includes receiving monitoring data representing one or more substantially real time electrical signals based on measurements from one or more respective electrodes. The method also includes selecting at least one signal of interest (SOI) from the monitoring data, each selected SOI being associated with a respective anatomical location and storing SOI data in memory corresponding to each selected SOI. The method also includes quantifying changes between signal characteristics of real time signals acquired for one or more respective anatomical locations and the at least one SOI that is associated with each of the respective anatomical locations. An output can be generated (Continued)

based on the quantifying to characterize spatially local signal changes with respect to each of the respective anatomical locations.

25 Claims, 5 Drawing Sheets

(51) Int. Cl.
*A61B 5/04* (2006.01)
*G16H 40/63* (2018.01)

(56) References Cited

U.S. PATENT DOCUMENTS

| | | | |
|---|---|---|---|
| 2009/0192393 A1 | 7/2009 | Hayam et al. | |
| 2011/0144713 A1 | 6/2011 | Bohn et al. | |
| 2012/0046564 A1* | 2/2012 | Koh | A61B 5/0422 600/515 |
| 2012/0089038 A1* | 4/2012 | Ryu | A61B 5/046 600/515 |
| 2013/0066221 A1 | 3/2013 | Ryu | |
| 2013/0116681 A1* | 5/2013 | Zhang | A61B 18/1206 606/34 |

OTHER PUBLICATIONS

International Search Report and Written Opinion, International PCT Application No. PCT/US2015/047499; filed Aug. 28, 2015; Date of Completion: Dec. 8, 2015; Authorized Officer: Ja Young Kim; 9 pgs.
Chinese Application for Invention No. 201580046310.X—filed Aug. 28, 2015; Applicant: CardioInsight Technologies, Inc.; Chinese Office Action; dated Mar. 26, 2019; 23 pp.

* cited by examiner

SIGNAL CHARACTERIZATION TO FACILITATE THERAPY DELIVERY

CROSS-REFERENCE TO RELATED APPLICATION

This application claims the benefit of U.S. provisional patent application No. 62/043,786 filed on Aug. 29, 2014 and entitled SIGNAL CHARACTERIZATION, which is incorporated herein by reference in its entirety.

TECHNICAL FIELD

This disclosure relates to characterizing electrophysiological signals such as to facilitate delivery of therapy.

BACKGROUND

Accurate diagnosis and treatment of cardiac arrhythmias can be important to maintain a healthy heart for properly pumping blood. There are many types of arrhythmias that may require treatment, such as ablation therapy (e.g., catheter ablation, such as radio frequency or cryoablation) and/or other therapies (e.g., drugs, pacemaker, defibrillator, etc.). In some cases electrophysiologists rely ultimately on their training and experience to apply the therapy, which may add subjectivity to the procedure.

SUMMARY

This disclosure relates to characterizing electrophysiological signals such as to facilitate delivery of therapy.

As one example, a method includes receiving monitoring data representing one or more substantially real time electrical signals based on measurements from one or more respective electrodes. The method also includes selecting at least one signal of interest (SOI) from the monitoring data, each selected SOI being associated with a respective anatomical location and storing SOI data in memory corresponding to each selected SOI. The method also includes quantifying changes between signal characteristics of real time signals acquired for one or more respective anatomical locations and the at least one SOI that is associated with each of the respective anatomical locations. An output can be generated based on the quantifying to characterize spatially local signal changes with respect to each of the respective anatomical locations.

As another example, a system includes memory and a processor. The memory is configured to store executable instructions and data. The data includes monitoring data representing one or more substantially real time electrical signals based on measurements from one or more respective electrodes. The processor is configured to access the memory and execute the instructions. The instructions include a selector configured to select at least one signal of interest (SOI) from the monitoring data to store SOI data in the memory for each selected SOI. Each selected SOI can be associated with a respective anatomical location. A signal analyzer is configured to compute signal characteristics for each of the SOIs based on the stored SOI data and for real time signals acquired for one or more respective anatomical locations. The signal analyzer also is configured to provide analysis data that quantifies changes in the computed signal characteristics. An output generator is configured to generate an output based on the quantifying.

DETAILED DESCRIPTION

This disclosure relates to characterizing signals and signal changes, such as to facilitate the diagnosis and/or treatment of a cardiac rhythm disorder. Systems and methods disclosed herein analyze signals across an anatomic region to identify, monitor and characterize one or more signals of interest (SOIs). The analysis can be utilized to identify a target site for delivering therapy and/or indicate an endpoint for such therapy delivery. The characteristics for each of a plurality of SOIs, corresponding to anatomical locations within the patient, further can be evaluated to provide a weighted assessment of prospective targets, either individually or by grouping the SOIs into respective tiers based on the assessment.

In some example embodiments, the combined use of noninvasive and invasive mapping information can be utilized to identify, monitor and characterize signals of interest. As one example, a plurality of SOIs at corresponding anatomical locations across an anatomical region within the patient's body can be determined based on analysis of reconstructed electrical signals. The reconstructed electrical signals across the anatomical region can be computed from signals acquired non-invasively by electrodes positioned outside the patient's body. The SOI's can be employed to navigate a therapy delivery device to the corresponding anatomical locations for a selected set of the SOI's. The therapy delivery device can thus be controlled to deliver therapy based on the analysis of stored SOI data and real time sensed signals (e.g., acquired by the delivery device or another sensor device) associated with the delivery device. The non-invasively acquired signals used to generate the SOI data can be acquired at any time up to delivery of the therapy.

Figure 1:
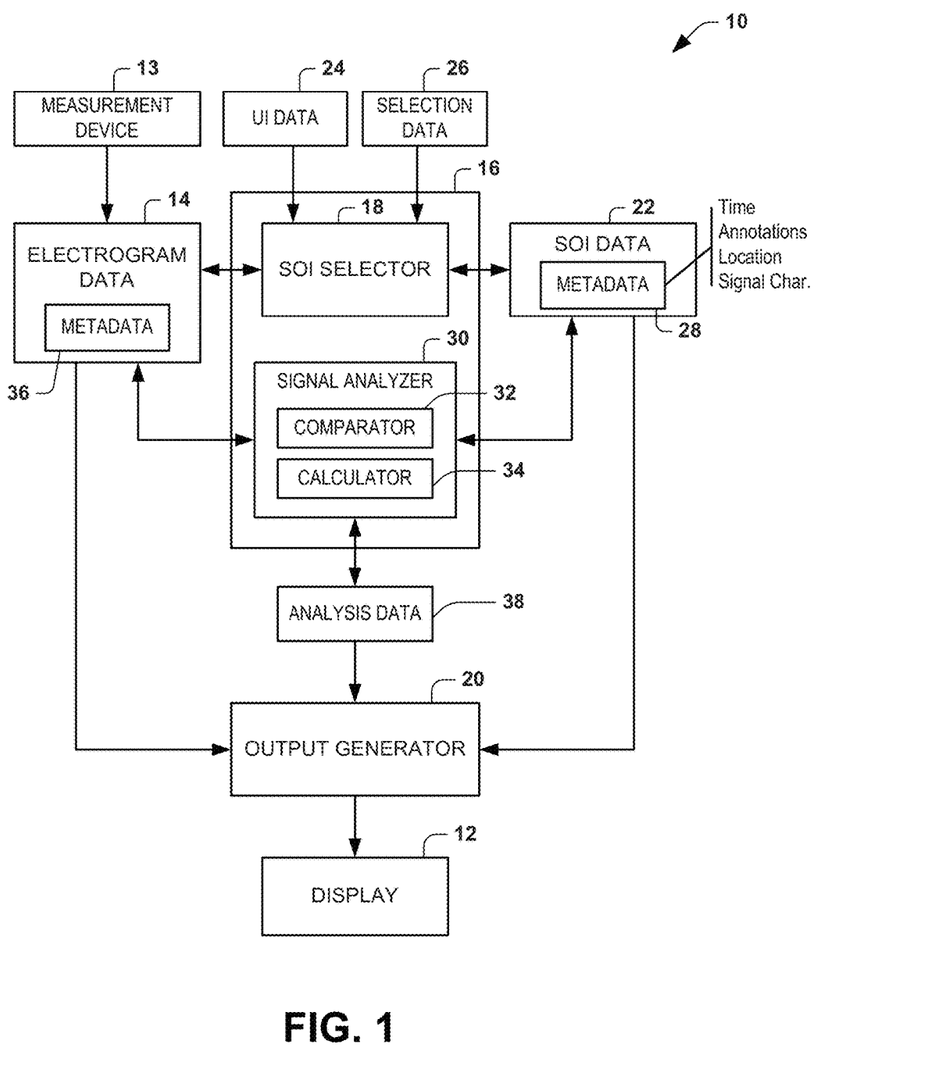
FIG. 1 depicts an example of system to characterize electrophysiological signals and changes between such signals.

FIG. 1 depicts an example of a characterization system that can be employed to characterize local signals. The system 10 can provide an output to a display 12 that includes a graphical representation of real time signals from current measurements and static signals for one or more signals of interest (SOIs) from prior saved measurements.

The system 10 can be implemented as machine readable instructions that are stored in a memory and executable by a computer. The memory could be implemented, for example, as one or more non-transitory computer readable media, such as volatile memory (e.g., random access memory), nonvolatile memory (e.g., a hard disk drive, a solid-state drive, flash memory or the like) or a combination thereof. The memory can be in a common storage device or be distributed. In some examples, the memory can be non-volatile memory (e.g., a buffer) to enable substantially real time analysis and/or display of such stored data. The computer can include a processing unit that can access the memory and execute the machine readable instructions. The processing unit can include, for example, one or more processor cores.

The system 10 includes a signal interface configured to receive and process measured electrical signals to provide corresponding electrogram data 14. The electrogram data 14 can be provided by or derived from measurements made by a measurement system, which can include at least one measurement device 13. The input signals utilized by the system 10 can be stored in memory (e.g., RAM) as real time electrogram data 14 based on measurements from one or more respective electrodes. As disclosed herein, the electrodes can be invasive (for direct measurements within a patient's body) and/or non-invasive (e.g., body surface measurements on the patient's skin surface). The signals thus can be invasively acquired signals provided by the measurement device 13 directly from one or more anatomical allocations within the patient's body to provide the electrogram data 14. Additionally or alternatively, the measurement device 13 can non-invasively measure electrical signals from a body surface of the patient outside of the patient's body. Such non-invasive measurements can be transformed into reconstructed electrograms for a surface inside the patient's body by solving the inverse problem to provide the electrogram data 14, such as disclosed herein.

The electrogram data 14 can be accessed by an output generator 20 to display the electrograms and related information (e.g., metadata 36) for monitoring on the display 12. For example, the output generator 20 generates the display 12, which can include a continuously refreshing dynamic representation of the one or more real time signals (e.g., electrograms) corresponding to the data 14 that are being acquired in real time from a set of one or more electrodes (e.g., non-invasively and/or invasively) applied to the patient. As will be described herein, the output generator can also display one or signals of interest (SOIs) and related electrical characteristics computed based on the electrogram data 14.

As used herein, in the context of the signals that are provided as the electrogram data 14, the term "real time" refers to an actual time when the signals are being acquired or displayed via the system 10, such as provided or derived from signals measured by the measurement device 13. In this way, a first set of signals acquired during a monitoring phase of an electrophysiology study are considered real time when acquired and/or interactively viewed on a display during such study. Additionally, signals acquired (by the same or different set of electrodes) during a subsequent diagnosis or treatment phase, would also be considered real time signal commensurate with the acquisition and/or time of display and user interaction with such signals. Thus, real time can reference acquisition time, viewing time and/or time of user interaction with such signals as they are collected and processed.

A signal characterization system 16 can include a signal of interest (SOI) selector 18 that is configured to select one or more SOIs, such as can be selected from the electrogram data 14. As mentioned, the electrogram data 14 can include a previously acquired set of electrograms for a plurality of anatomic locations at one or more regions of the patient's heart. The electrogram data 14 can also include real time electrograms currently being acquired by the associated measurement device 13 for one or more anatomic locations of the patient's heart.

The SOI selector 18 can generate corresponding SOI data 22 representing each of one or more selected SOIs, which can be stored in memory. The SOI data thus can be a proper subset of the electrogram data 14. For example, the SOI selector 18 can select one or more time intervals of the real time signals being acquired (and stored as electrogram data) for respective anatomic locations in response to a user input. In the example of FIG. 1, the user input is represented as UI data 24, which can be generated in response to a user interacting with an interactive portion of the display (e.g., via a graphical user interface GUI) in which respective signals are displayed for a plurality of different anatomic locations. In some examples, the output generator can display a plurality of signals for respective anatomic locations based on electrogram data previously generated for such locations, such as during an earlier of phase of a current study or during another prior EP or other study for the given patient.

In another example, the SOI selector 18 can automatically select one or more SOIs from the real time signals (e.g., corresponding to the data 14) to provide the SOI data 22 based upon selection data 26. For example, the selection data 26 can correspond to one or more anatomical landmarks or predefined locations, corresponding to an anatomic region, which that can be programmable in response to a user input. For instance, the selection data 26 can define a plurality of anatomical locations (e.g., landmarks or a region surrounding a landmark) or coordinates in a three-dimensional coordinate system of interest at which one or more SOI at such locations can be selected at one or more time intervals. The SOI for such predefined location(s) can be selected at the beginning of a procedure, in response to an event being detected during a procedure or from another predetermined time period, such as from a previous study. For example, the SOIs can define a set of signals for locations spatially distributed across a predetermined anatomic region of the patient's heart. The corresponding selected time intervals of each SOI can be stored in the SOI data 22 for further processing, as disclosed herein.

As yet another example, one or more SOIs can be from a different encounter with a given patient (e.g., a previous EP study). For instance, the electrogram data 14 for the patient can be retrieved from a patient's electronic medical record (EMR) or other database in which the SOIs can be stored within the electrogram data 14, such as disclosed herein.

As a further example, the user input data 24 can correspond to a selection made by a user in response to a user input (e.g., activating a button or other form of graphical user interface (GUI)). Activation of such GUI thus can cause a snapshot of a corresponding time segment of the selected SOI to be captured and stored in the SOI data. In addition to the static graphical representation of the signal, including measurement data for the SOI sampled at a sampling frequency over the selected time interval, being stored in memory, the SOI selector 18 can also store corresponding metadata 28 that is programmatically linked with such measurement data for a respective SOI. For example, the metadata 28 for a given SOI can include data identifying a time associated with the SOI (e.g., a beginning time for the SOI, a time interval having a start and end time or a series of time stamps). The metadata can also include location data for programmatically linking the respective SOI to a corresponding spatial location, such as can correspond to a position in a 3-D coordinate system that has been registered to the patient's anatomy or another coordinate system. The metadata 28 can also include the results of signal analysis for each SOI, such as calculated signal characteristics as disclosed herein.

The metadata 28 can also include other user-specified information (e.g., in response to user input data 24), which can include a relative ranking of each of the SOI's based on ranking criteria. For instance, the SOI selector 18 can employ one or more calculators 34 to compute values of respective signal characteristics (e.g., cycle length, disorganization, fractionation, percentage of activation), such as described below. The signal analyzer 30 can aggregate the values computed for each of a plurality of signal characterization calculators 34 for each SOI to generate a corresponding score for each SOI. The scores can be used to rank each of the SOIs into a relative order that is relevant to application of a therapy. In some cases one or more default or user-defined thresholds can be employed to classify the SOIs into two or more groups. For the example of two groups, the signal analyzer can rank each of the SOIs based on its associated score to classify a first subset of the SOI's within the region as high priority SOIs and to classify each other subset of the plurality of anatomical locations as low priority SOIs. The high priority SOIs can thus define target anatomic locations for applying therapy (e.g., based on SOI metadata specifying locations for each SOI, such as spatial coordinates). Similarly, the low priority SOIs can identify areas to which therapy can be applied late or omitted altogether.

When two or more signal characteristics are computed, the respective characteristics can be weighted to afford greater relative importance to different ones of the computed values. Such weighting can be applied by the calculator 34 automatically to default weighting or as specified by a user in response to a user input (e.g., in UI data 24).

The output generator 20 can also employ the ranking of SOIs to control the visualization in the display, such as by setting a position of each of the SOI visualizations presented in the output display, for example. As an example, a user can rank each of the SOI's individually in response to a user input. As another example, a user can rank within a group of SOI's. For instance, a user can selectively group SOI's spatially (e.g., according to the location of the SOI on an anatomic region of the patient's heart) and/or temporally (e.g., according to a time or an event that has occurred) into separate groups. When SOI's are grouped, a user can also rank the individual SOI's within each group. For example, a user can rank the SOI groups for the entire atria (spatially) or the SOI's associated with a particular clinical therapy (e.g., pacing pulse or ablation therapy) that is applied (temporally). The ranking can be used to prioritize intracardiac targets for delivery of treatment.

In some examples disclosed herein, the electrogram data 14 includes a combination of reconstructed electrograms based on non-invasively acquired electrical signals, as disclosed herein, and invasively acquired intracardiac electrograms, such as via a catheter or other intracardiac electrodes. In such an example, employing both intracardiac and non-invasive information, a user can manually define a relative weighting between intracardiac and non-invasive information in response to a user input (e.g., UI data 24). The resulting order can be utilized to prioritize targets for delivery of treatment at such target sites corresponding to the anatomic locations for each of the electrograms (e.g., stored in the analysis data 38 and/or as part of the metadata 36). Additionally, the output generator 20 can generate the output visualization would to display the priority of all regions of heart, based on weighting of invasive and non-invasive information. The weighting and associated priority can be displayed graphically via color coding on a graphical map of the heart and/or in an order list of the target sites.

As mentioned, the signal analyzer 30 is configured to analyze the one or more real time signals corresponding to the real time electrogram data 14 as well as the SOI represented by the SOI data 22. The signal analyzer 30 can include a comparator 32 programmed to compare the one or more real time signals (e.g., represented by the real time electrogram data 14) with one or more of the selected SOIs for each corresponding time segment for which the SOI has been captured. The comparator 32 can also quantify changes or differences between the respective signals or derived signal characteristics of such signals being analyzed based on the comparisons. The changes can include quantifying changes between the respective real time signals and the stored SOIs as well as differences between the metadata (e.g., values of any signal characteristics computed by calculator 34) that may have been computed for each of the respective real time and static signals corresponding to the SOI data 22.

To determine the signal characteristics available for processing by the comparator 32, each of the one or more calculators 34 is configured to compute one or more characteristics for the respective signals, including the real time signals 14 and the SOIs corresponding to SOI data 22. In some examples, the signal characteristics for the SOIs can be precomputed and stored as part of the metadata 36. In other cases, the signal characteristics for the SOIs and the real time signals can be computed concurrently.

As an example, the calculator 34 can be programmed to compute an activation time for each of a plurality of periods of corresponding electrograms corresponding to the real time electrograms 14 or the static electrograms provided by the SOI data 22. For instance, the activation time for each electrogram (e.g., for SOIs and real time acquired data) can be calculated using a dv/dt method or another method.

The calculator 34 can also be programmed to compute an indication of cycle length for the signals, such as based on a difference between adjacent activation times over a corresponding time interval that includes a plurality of electrogram pulses. For example, the cycle length can be computed as an average cycle length for beats that occur over a corresponding time period (e.g., time segment), such as corresponding to the period of time for which the SOI has been captured. It is understood that the time period for a segment of a given SOI can be set in response to a user input or be fixed to a default duration value. For example, the time period can correspond to the duration of time that is capable of being displayed on the display 12 by the output generator 20, which can be fixed or variable.

As a further example, the calculator 34 can be programmed to compute a percentage of activation time for each of the respective signals. The calculator can also compute fractionation for electrograms in the electrogram data (e.g., for SOIs and real time electrograms). For example, the calculator can compute fractionation value based on voltage, frequency and phase of each of the electrograms. Those skilled will understand and appreciate other computations that can be performed by the calculator 34 to compute corresponding signal characteristics that can be stored in metadata 28 and 36. Examples of other computations that can be implemented by the calculator 34 are disclosed in International Application No. PCT/US2011/059174, which is incorporated herein by reference. Thus, it is understood that the calculator 34 can compute one or more indices representing an indication of synchrony for a predefined region or more globally across two or more regions (e.g., different chambers of the heart) based on the signals represented by the data 14 and 22.

Based on the analysis performed by signal analyzer 30, including comparisons, calculations and/or ranking, the signal analyzer can provide corresponding analysis data 38. As mentioned, some of the resulting analysis data 38 can also be stored as metadata in the electrogram data 14 and the SOI data 22. In order to facilitate the comparator 32 the real time electrogram data can refresh at a predefined rate which can be set to a default value of a user programmable in response to a user input. Associated weighting that is applied by the signal analyzer to the real time electrograms and SOIs as well as to the computed signal characteristics, as disclosed herein, can also be stored in the associated metadata.

The signal analyzer 30 thus can perform its analysis (e.g., calculations by calculator 34 and comparisons by comparator 32) with respect to the real time electrogram data 14 and the SOI data 22 in substantially real time with each refresh of the real time electrogram data. Since the output generator 20 currently displays both real time electrogram data and SOI data 22 in the display 12, visual comparison between the current real time data and the data that has been selected and stored in memory can be facilitated by the user. A user can also pause or bookmark one or more signals being visualized in the display 12 in response to a user input to enable further time for visual inspection of such signal.

It is to be understood and appreciated that the real time signals can correspond to electrogram signals measured invasively by a probe having one or more electrodes disposed thereon, such as an EP catheter or an ablation catheter that may be inserted within the patient's body. Additionally or alternatively, the real time signals can correspond to reconstructed electrograms that are computed based on non-invasive electrical measurements from the patient's body such as can be computed by solving the inverse problem as is known in the art. As one example, the reconstructed electrograms can be computed according to the principles disclosed in U.S. Pat. No. 7,983,743.

In addition to the output generator 20 producing a display corresponding to a visual representation of the respective electrogram signals based on the real time electrogram data 14 concurrently with a visual representation of the static SOI data 22, the output generator can also generate one or more maps or other forms of output data corresponding to the metadata 28 and 36 for the respective signals, such as disclosed herein. Additionally, in other examples, the signal analyzer 30 can provide the analysis data 38 to provide an indication of an endpoint for delivery of a therapy. The indication of the endpoint can be determined based upon a comparison between the respective real time signals (corresponding to the data 14) and one or more SOI signals (corresponding to the data 22), which are being presented on the display 12. Additionally or alternatively, the indication of the endpoint can also be determined based upon a comparison between metadata (e.g., values computed by calculator 34) 36 for the respective real time signals and corresponding metadata 28 for one or more SOIs represented in SOI data 22.

The output generator 20 can also produce the display to visualize both targets (e.g., rotors, focal points or regions, fast-firing signals) determined based on non-invasively acquired measurements in combination with the invasively acquired SOI information. The targets can be identified, for example, based on ranking, statistical index, or the like of the SOIs. The visualization further can display the priority of all regions of heart, based on a relative weighting of the invasive and non-invasive information that has been generated. The associated endpoint for delivery of treatment for each target site further can be computed based on the signal analyzer 30 comparing the changes between the local real time signals and nearest neighboring SOIs. For example, a user can navigate a delivery device to high priority target sites, as defined by analyzer for SOIs) to deliver treatment at such sites and deliver therapy at such site until a predefined cutoff threshold is reached. The cutoff threshold can be compared to the difference computed by comparator 32 between the measured real time signal at the target site and the SOI values (e.g., metadata).

Figure 2:
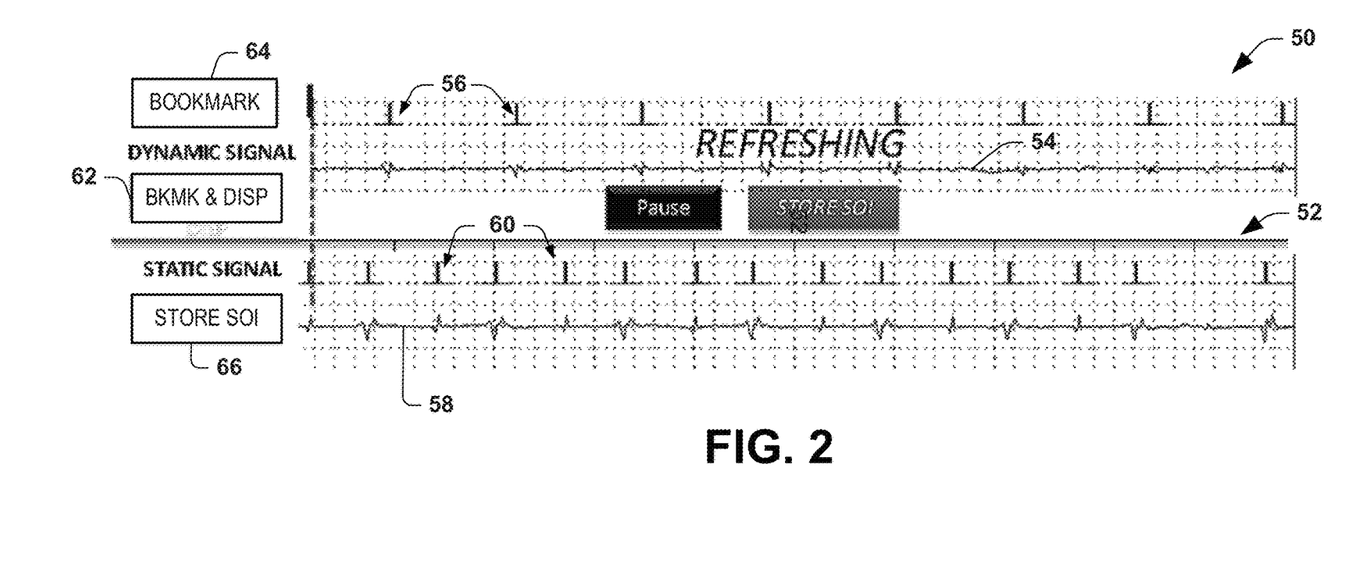
FIG. 2 depicts an example of a user interface that can be generated for characterizing signals.

FIG. 2 depicts an example of an output display (or a portion thereof) that can be generated (e.g., by output generator 20 of FIG. 1). The output can be an interactive display that includes GUI features that can be selectively activated in response to user inputs to programmatically to capture and store signals and compute corresponding metadata. As an example, the output includes a dynamic signal 50 and a static SOI demonstrated at 52. The dynamic signals 50 can correspond to a real time input measurement (e.g., an electrogram derived from measurements from one or more electrodes, invasively or non-invasively positioned) that is continuously refreshing at a refresh rate such as disclosed herein. In addition to displaying real time electrograms, as demonstrated at 54 and 58, analysis of each of the respective signals 50 and 52 (e.g., by signal analyzer 30) can also produce signal metadata, such as disclosed herein.

In the example of FIG. 2, each of the signals 50 and 52 also includes activation times 56 and 60 computed (e.g., by calculator 34) for each signal period. The static signal 52 thus demonstrates an electrogram for an SOI that can be selected (e.g., in response to a user input or automatically) along with a plot of activation times 60 computed for the selected SOI. By displaying the dynamic signal and static signals for the SOI adjacent to each other in the display, a visual comparison of changes can easily be made by the user.

During operation, the static signal or SOI 52 can be identified and bookmarked in response to a user selecting a "BKMK & DISP" GUI element 62. In other examples, the user may wish to bookmark without viewing a segment of the real time signal which can be stored in memory (e.g., as the SOI data 22) in response to activating a "BOOKMARK" GUI button 64. While the real time signal is refreshing, a user can also pause the signal (e.g., via a "pause" GUI element) to stop the refreshing and thereby spend additional time visually inspecting the recent dynamic signal and corresponding signal characteristics 56 relative to the signal 58 and its computed signal characteristics 60. In some cases, a user can further store the SOI into memory (e.g., non volatile memory) by activating a "STORE SOI" button GUI element 66. In response to storing the SOI, corresponding metadata can also be stored and programmatically linked with the data representing the signal characteristics, as disclosed herein.

Figure 3:
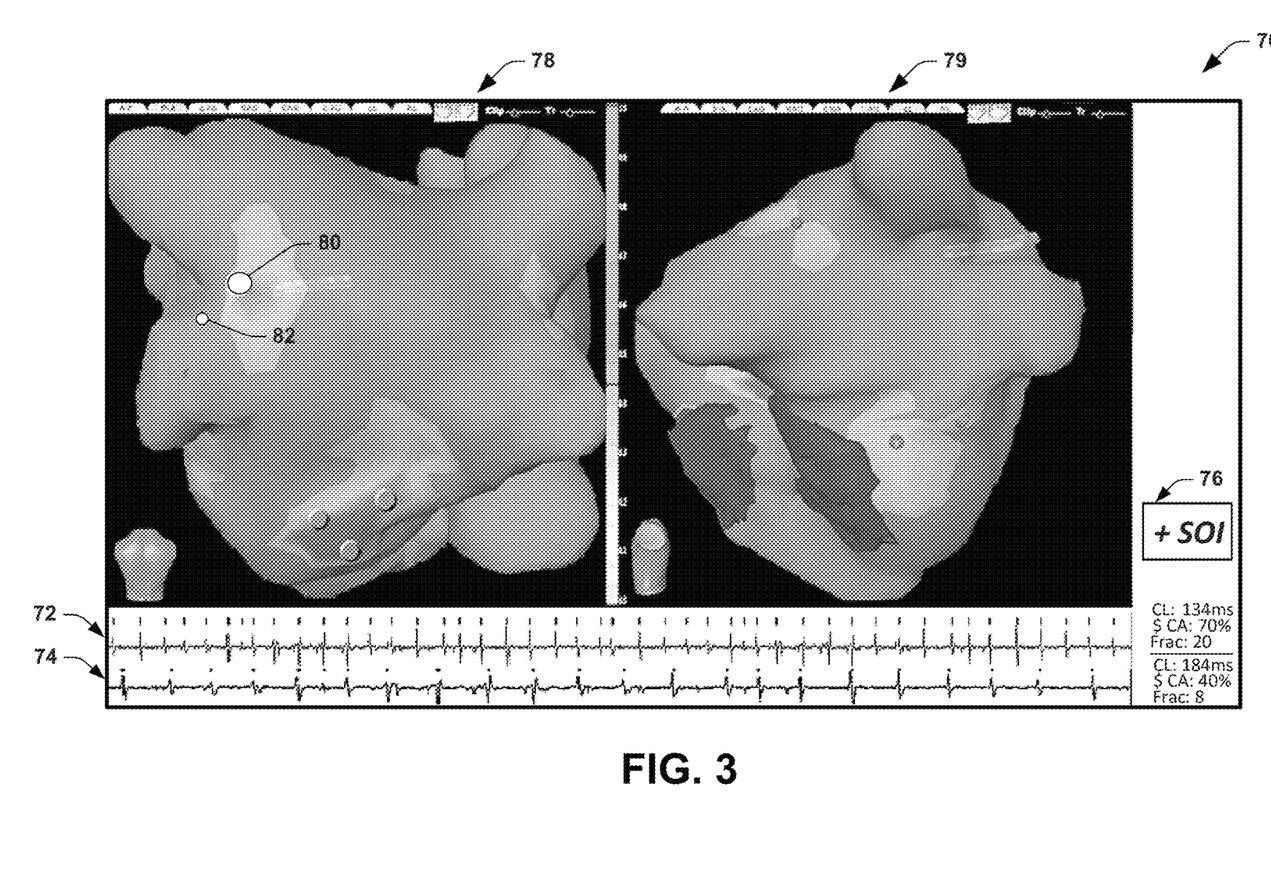
FIG. 3 depicts another example of a user interface that can be generated for characterizing signals.

FIG. 3 depicts an example of another interactive output display 70 that can be generated (e.g., by output generator 20 of FIG. 1). In the example of FIG. 3, the display 70 includes static and dynamic signals of interest 72 and 74, respectively. The output also includes graphical maps 78 and 79 showing different views of a heart model. The graphical maps 78 and 79 also include indicia (e.g., markers, such as virtual electrodes) 80 and 82 representing different spatial SOIs for the signals 72 and 74, respectively, presented in the output 70. The example maps 78 and 79 demonstrate arrhythmia drivers, such as can be computed from electrical measurements obtained non-invasively and/or invasively from a patient. Other types of maps can be displayed, such as in response to a user input. Different views of the maps 78 and 79 can also be displayed via tabs or other user inputs.

Additionally, while two SOIs are shown in FIG. 3, additional SOIs could be added to the display via GUI element 76, which can be activated in response to a user input. The output display can also provide corresponding GUI elements for bookmarking and storing data associated with the respective signals. In addition to the GUI elements for the interactive output display 70, the output generator can also present representation of metadata for signal characteristics that can be computed (e.g., by calculator 34) for each of the static and dynamic signals 72 and 74, respectfully. In this case, the metadata is displayed adjacent the signals 72 and 74, to indicate computed signal characteristics including cycle length, percentage continuous activation and fractionation. In other examples, other calculations could also be used. Thus by computing these signal parameters for a plurality of different signals, including a static SOI that is selected as disclosed herein and a dynamic signal such as corresponding to the real time signal being collected via probe or reconstructed electrogram, a comparison can be made visually by the user to facilitate treatment and deliver the therapy, for example. Automated comparisons can also be implemented (e.g., by signal analyzer 30) between the SOIs and real time signals.

Other interactive features can also be implemented in the output display. For example, a user can also enter annotated notes or to provide a comparative example spatially distributed and/or temporally distributed over time during the procedure. When multiple SOIs are shown, the SOIs can also be ranked (e.g., in order of target priority) and listed in a corresponding order. The ranked order of SOIs thus can be used to identify corresponding target anatomic locations in the graphical maps 78 and 79 (e.g., numbered indicators overlaid on the maps) and to facilitate navigation of a therapy delivery device to each such target. The user can then employ a localization system to position the therapy delivery device at a selected target.

By analyzing and/or characterizing SOIs at one or more regions of interest over one or more time intervals, a user can visualize signal characteristics to help quantify changes between the real time signal and one or more of the SOIs. Additionally or alternatively, the signal analyzer 30 can compute comparative statistics or other information to quantify changes between the real time signal and one or more of the SOIs, such as based on the metadata stored for such signals and/or other computations. The output display 70 can also include additional windows or tabs that can correspond to noninvasive signal characterizations or maps generated from noninvasive signals that may be utilized in conjunction with invasive procedures such as a mapping or ablation catheters.

Figure 4:
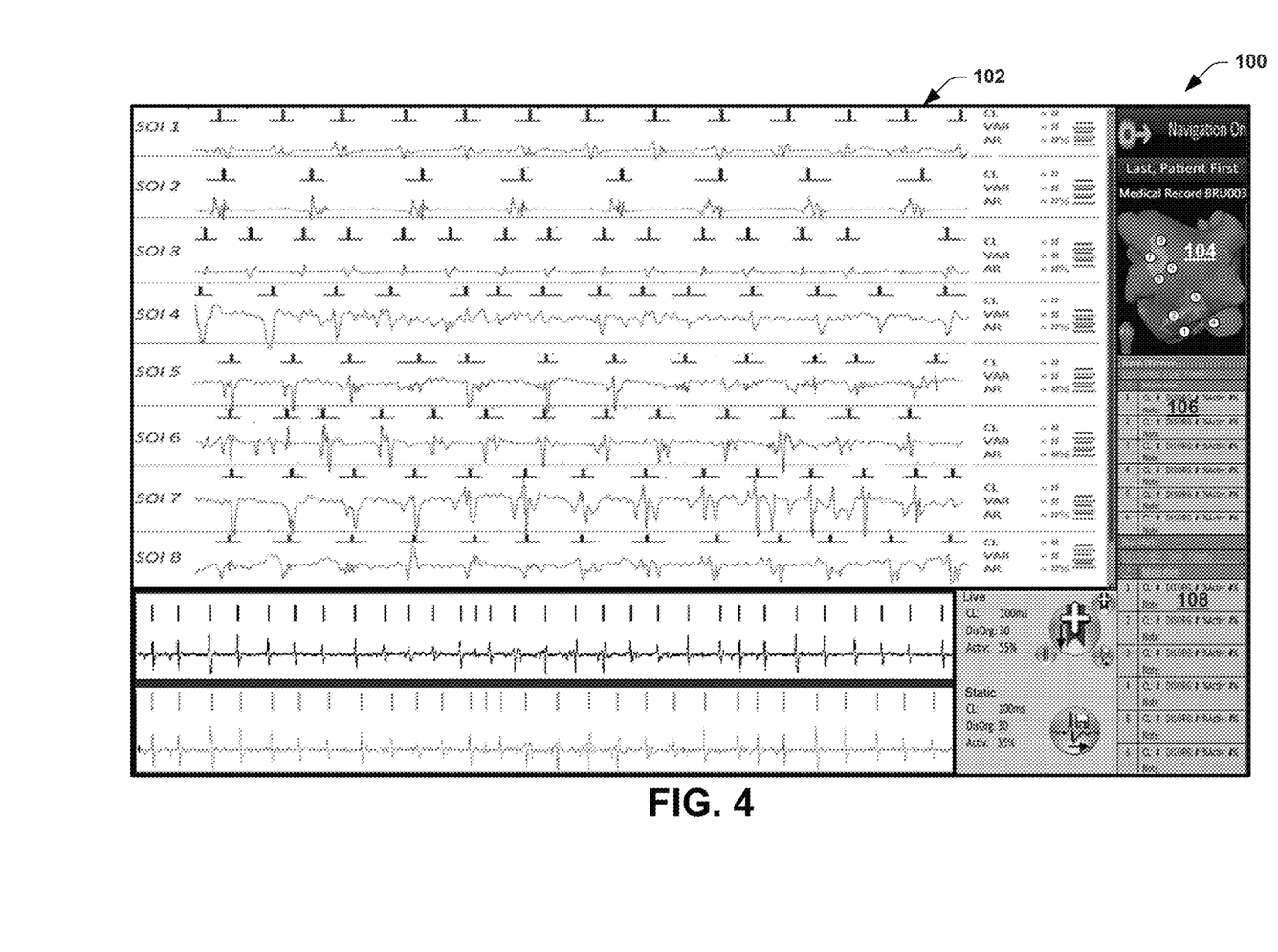
FIG. 4 depicts yet another example of a user interface that can be generated for characterizing signals.

FIG. 4 demonstrates an example of another interactive output display 100 that includes a given dynamic signal that is displayed concurrently with a plurality of different SOIs 102, along with corresponding tables 106 and 108 visualizing selected metadata each respective signal. It is to be understood and appreciated that each SOI can correspond to a different spatial location that has been determined in patient geometry (e.g, 3D spatial coordinates). In other examples, some or each of the SOIs may correspond to a common spatial location but signals captured at different times, or a combination of different spatial locations and different time intervals for such SOIs.

Similar to FIG. 3, the display can include a graphical map 104 of patient anatomy (e.g., the heart), which further can include indicia 105 superimposed on a graphical model of the anatomy. The indicia 105 demonstrate the spatial location corresponding to each of the respective SOI. The output display 100 can also include a table 106 to demonstrate results of corresponding signal analysis (e.g., signal analyzer 30 of FIG. 1) based on metadata (e.g., metadata 28 and 36). In the example demonstrated in FIG. 4, the metadata in the table 106 for the different SOI includes user notes, cycle length, disorganization, and percent of activation. In the example of FIG. 4, a separate table 108 is demonstrated for bookmarks that may not be SOIs. The notes can be entered into fields of each table 106 and 108, e.g., via transcription or via keyboard or other user input device, to record observations or other clinically relevant information for each SOI or each bookmark that may have been placed. It is understood and appreciated that one or more SOI can be automatically generated or generated in response to the user input such as disclosed herein. Depending on the number of entries and size of each table, GUI elements can be employed to scroll through the entries.

As a further example, the SOI waveforms and activation times can be determined based on reconstructed electrograms that have been generated from noninvasive body surface signals. Additionally or alternatively, some can be from noninvasive signals while others can be from invasive signals, such as from one or more electrodes on a catheter probe. Also demonstrated in the anatomical model can be a graphical representation of a probe containing electrodes, with the probe positioned on the heart model at a position and orientation corresponding to a current location of the electrodes. The current location of the electrodes and the probe carrying the electrodes can be determined based on employing a localization engine, which can implement a conventional or proprietary localization method to enable navigation of a therapy delivery device to target anatomic locations corresponding to SOIs, such as according to the ranked order of priority for the SOIs. As a further example, a user can select an entry in the table 106 or 108, which can result in highlighting of the entry and/or identifying corresponding indicia at a corresponding anatomical location on the graphical map 104 that has been linked (via metadata 28 or 36) for the selected entry.

Figure 5:
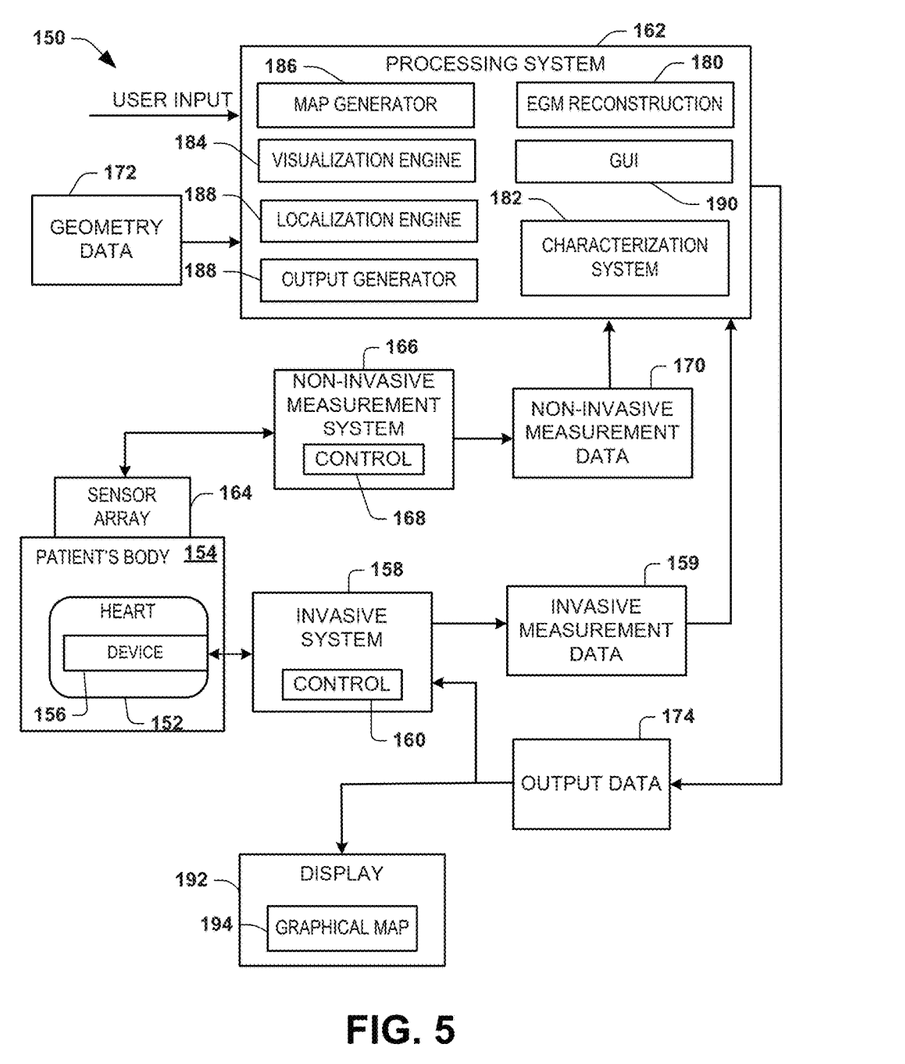
FIG. 5 depicts an example of a system.

FIG. 5 depicts an example of a system 150 that can be utilized for characterizing local signals. The system 150 can be employed in conjunction with performing diagnostics and/or treatment of a patient. In some examples, the system 150 can be implemented to generate corresponding graphical outputs for signals and/or graphical maps for a patient's heart 152 in real time as part of a diagnostic procedure (e.g., identifying, monitoring and/or characterizing of signals during an electrophysiology study) to help assess the electrical activity and identify arrhythmia drivers for the patient's heart. Additionally or alternatively, the system 150 can be utilized as part of a treatment procedure, such as to help a physician determine parameters for delivering a therapy (e.g., delivery location, amount, duration and type of therapy) and provide a visualization to facilitate determining when to end the procedure for each target location.

For example, an invasive system 158 can include one or more intracardiac devices 156 affixed thereto. The intracardiac device(s) can be inserted into a patient's body 154 as to contact the patient's heart 152, endocardially or epicardially. The placement of the device 156 can be guided via a localization engine 188 and delivery mechanism. The guidance can be automated, semi-automated or be manually implemented based on information provided, such as to position the delivery device at one or more SOIs. Those skilled in the art will understand and appreciate various type and configurations of devices 156 and localization techniques that can be implemented by the localization engine

188, which can vary depending on the type of treatment and the procedure. The localization engine 188 thus can localize the device 156.

For example, the device 156 can include one or more electrodes disposed thereon at predetermined locations that are configured to measure electrical activity. Each such electrode can be positioned with respect to the heart to sense electrical activity, such as corresponding to real-time electrograms for the patient's heart. The invasive system 158 can include a control 160 configured to process (electrically) and control the capture of the measured signals as to provide corresponding invasive measurement data 159.

By way of further example, the device 156 can be configured to deliver therapy, such as to ablate tissue (e.g., providing electrical therapy, chemical therapy, sound wave therapy, thermal therapy or any combination thereof). As one example, the device 156 can include one or more electrodes located at a tip of an ablation catheter configured to generate heat for ablating tissue in response to electrical signals (e.g., radiofrequency energy) supplied by the system 158 according to controls. In other examples, the therapy delivery device 156 can be configured to deliver cooling to perform ablation (e.g., cryogenic ablation), to deliver chemicals (e.g., drugs), ultrasound ablation, high-frequency ablation, or a combination of these or other therapy mechanisms. In still other examples, the therapy delivery device 156 can include one or more electrodes located at a tip of a pacing catheter to deliver electrical stimulation, such as for pacing the heart, in response to electrical signals (e.g., pacing pulses) supplied by the system 158. Other types of therapy can also be delivered via the system 158 and the invasive therapy delivery device 156 that is positioned within the body. The same device can be used for measuring electrical signals and delivery of therapy or, in other examples, multiple devices can be utilized together to measure electrical signals and deliver therapy.

As a further example, the system 158 can be located external to the patient's body 154 and be configured to control therapy that is being delivered by the device 156. For instance, the system 158 can also control electrical signals provided via a conductive link electrically connected between the delivery device (e.g., one or more electrodes) 156 and the system 158. The control system 160 can control parameters of the signals supplied to the device 156 (e.g., current, voltage, repetition rate, trigger delay, sensing trigger amplitude) for delivering therapy (e.g., ablation or stimulation) via the electrode(s) to one or more location of the heart 152. The control circuitry 160 can set the therapy parameters and apply stimulation based on automatic, manual (e.g., user input) or a combination of automatic and manual (e.g., semiautomatic) controls. One or more sensors (not shown) can also communicate sensor information back to the system 158.

The position of the device 156 relative to the heart 152 can be determined and tracked intraoperatively via an imaging modality (e.g., fluoroscopy, xray), a processing system 162, direct vision, or an electromagnetic localization system or the like. The location of the device 156 and the therapy parameters thus can be combined to help control therapy. Additionally, the application of therapy (e.g, manually in response to a user input or automatically provided) can cause a timestamp or other time identifier to be tagged (e.g., as metadata) to the measurement data to identify when the therapy is applied. Other metadata describing the therapy (e.g., type, delivery parameters etc.) can also be stored with the measurement data to help evaluate changes in electrophysiology in response to the therapy that is applied. The delivery of the therapy at each target delivery site (e.g., corresponding to SOIs) can be guided and a delivery endpoint specified for each site based on signal characteristics computed and analyzed, as disclosed herein.

Before, during and/or after delivering a therapy (e.g., via the system 158), one or more of the measurement systems 158 or 166 can be utilized to acquire electrophysiology information for the patient. In the example of FIG. 5, a sensor array 164 includes one or more electrodes that can be utilized for recording patient electrical activity.

As one example, the sensor array 164 can correspond to a high-density arrangement of body surface sensors (e.g., greater than approximately 200 electrodes) that are distributed over a portion of the patient's torso for measuring electrical activity associated with the patient's heart (e.g., as part of an electrocardiographic mapping procedure). An example of a non-invasive sensor array that can be used is shown and described in International application No. PCT/US2009/063803, filed 10 Nov. 2009, which is incorporated herein by reference. Other arrangements and numbers of sensing electrodes can be used as the sensor array 164. As an example, the array can be a reduced set of electrodes, which does not cover the patient's entire torso and is designed for measuring electrical activity for a particular purpose (e.g., an array of electrodes specially designed for analyzing AF and/or VF) and/or for monitoring and/or tracking electrophysiological signals for a predetermined spatial region of the heart.

As mentioned, one or more sensor electrodes may also be located on the device 156 that is inserted into the patient's body. Such sensors can be utilized separately or in conjunction with the non-invasive sensors 164 for mapping electrical activity for an endocardial surface, such as the wall of a heart chamber, as well as for an epicardial surface. In each of such example approaches for acquiring real time patient electrical information, including invasively via the device 156, non-invasively via the array 164, or a combination of invasive and non-invasive sensing, the real time sensed electrical information is provided to a corresponding measurement system 158, 166. Similar to the invasive system 158, the measurement system 166 can include appropriate controls and signal processing circuitry 168 for providing corresponding measurement data 170 that describes electrical activity detected by the sensors in the sensor array 164. The measurement data 170 can include analog and/or digital information (e.g., corresponding to electrogram data 14). Thus, the measurement data 159 and 170 can correspond to the electrogram data 14 of FIG. 1.

The control 168 can also be configured to control the data acquisition process (e.g., sample rate, line filtering, etc.) for measuring electrical activity and providing the measurement data 170. In some examples, the control 168 can control acquisition of measurement data 170 separately from the therapy system operation, such as in response to a user input. In other examples, the measurement data 170 can be acquired concurrently with and in synchronization with delivering therapy by the therapy system, such as to detect electrical activity of the heart 152 that occurs in response to applying a given therapy (e.g., according to therapy parameters). For instance, appropriate time stamps can be utilized for indexing the temporal relationship between the respective measurement data 159 and 170 and delivery of therapy, such as to facilitate the monitoring and signal analysis thereof.

The processing system 162 is programmed to combine the measurement data 159 and 170 corresponding to electrical activity of the heart 152 with geometry data 172 by applying appropriate processing and computations to provide corresponding output data 174. The output data 174 can represent or characterize electrical signals at any number of one or more spatial locations across a cardiac envelope (e.g., on a surface of the heart 152).

As disclosed herein (see, e.g., FIGS. 1-4), the output data 174 can represent one or more electrical signals and signal characteristics determined from the electrical measurement data 159 and 170 acquired for the patient over one or more time intervals. Specifically, the signals can include both real time dynamic signals that refresh over time (e.g., periodically) as well as one or more other localized static signals of interest (SOI). The output data 174 can include one or more graphical maps demonstrating electrical signal features determined with respect to a geometric surface of the patient's heart 152 two which such measurements correspond (e.g., from measurements obtained invasively and/or non-invasively).

Since, in some examples, the measurement system 166 can measure electrical activity of a predetermined region or the entire heart concurrently (e.g., where the sensor array 164 covers the entire thorax of the patient's body 154), the resulting output data 174 thus can also represent concurrent data for the predetermined region or the entire heart in a temporally and spatially consistent manner, such as to supply the user with a global view of the heart's electrical characteristics during such characterizing and application of therapy. The time interval for which the output data/maps are computed can be selected based on user input (e.g., selecting a time interval from one or more waveforms) and/or automatically.

Additionally or alternatively, the selected measurement intervals can be synchronized with respect to the application of therapy provided by the system 158, such as to record SOI at one or more selected spatial locations before and after application of therapy. The recorded SOI can also be localized spatially as to include one or more regions (e.g., a plurality of nodes) adjacent to the site where the therapy was delivered based on localization of the delivery site.

For the example where the electrical measurement data is obtained non-invasively (e.g., via body surface sensor array 164), electrogram reconstruction 180 can be programmed to compute an inverse solution and provide corresponding reconstructed electrograms based on the process signals and the geometry data 172. The reconstructed electrograms thus can correspond to electrocardiographic activity across a cardiac envelope, and can include static (three-dimensional at a given instant in time) and/or be dynamic (e.g., four-dimensional map that varies over time). Examples of inverse algorithms that can be utilized in the system 10 include those disclosed in U.S. Pat. Nos. 7,983,743 and 6,772,004, which are incorporated herein by reference. The EGM reconstruction 180 thus can reconstruct the body surface electrical activity measured via the sensor array 164 onto a multitude of locations on a cardiac envelope (e.g., greater than 1000 locations, such as about 2000 locations or more). In other examples, the output system 162 can compute electrical activity over a sub-region of the heart based on electrical activity measured invasively, such as via the device 156 (e.g., including a basket catheter or other form of measurement probe).

As disclosed herein, the cardiac envelope can correspond to a three dimensional surface geometry corresponding to a patient's heart, which surface can be epicardial or endocardial. Alternatively or additionally, the cardiac envelope can correspond to a geometric surface that resides between the epicardial surface of a patient's heart and the surface of the patient's body where the sensor array 164 has been positioned. Additionally, the geometry data 172 that is utilized by the electrogram reconstruction 180 can correspond to actual patient anatomical geometry, a preprogrammed generic model or a combination thereof (e.g., a model that is modified based on patient anatomy).

As an example, the geometry data 172 may be in the form of graphical representation of the patient's torso, such as image data acquired for the patient. Such image processing can include extraction and segmentation of anatomical features, including one or more organs and other structures, from a digital image set. Additionally, a location for each of the electrodes in the sensor array 164 can be included in the geometry data 172, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array, such as a digitizer or manual measurements.

As mentioned above, the geometry data 172 can correspond to a mathematical model, such as can be a generic model or a model that has been constructed based on image data for the patient. Appropriate anatomical or other landmarks, including locations for the electrodes in the sensor array 164 can be identified in the geometry data 172 to facilitate registration of the electrical measurement data 159 and 170 and storing corresponding spatial location information as metadata for such measurement data. The identification of such landmarks and can be done manually (e.g., by a person via image editing software) or automatically (e.g., via image processing techniques).

By way of further example, the geometry data 172 can be acquired using nearly any imaging modality based on which a corresponding representation of the geometrical surface can be constructed, such as described herein. Such imaging may be performed concurrently with recording the electrical activity that is utilized to generate the patient measurement data 170 or the imaging can be performed separately (e.g., before or after the measurement data has been acquired).

The system 150 can also include a signal characterization system 182, such as corresponding to the system 16 of FIG. 1. Thus, reference can be made to FIGS. 1-4 for additional context and functionality of the system 182. Briefly, the system 182 can include an SOI selector (e.g., selector 18) and signal analysis functions (e.g., analyzer 30) such as to provide output data 174 that includes both real time signals and one or more SOI (e.g., based on measurement data 159 and/or 170), which signals can be display concurrently on a display 192. The monitoring system 182 further can include a calculator configure to compute one or more signal characteristics for each SOI and for monitored real time signals provided by data 159 and/or 170. The characterization system 182 also performs comparative analysis of real time electrical signals and SOIs such as to facilitate identifying an endpoint to therapy that is being delivered via device 156.

Following or concurrently with providing the real time measurement data (e.g., via data 159 and/or 170) and prior SOI data, a map generator 186 can be programmed to generate graphic maps that can be part of the computed output data 174. Parameters associated with the displayed graphical representation, corresponding to an output visualization of the computed map, such as including selecting a time interval, a type of information that is to be presented in the visualization and the like can be selected in response to a user input via a graphical user interface (GUI) 190. For example, a user can employ the GUI to selectively program one or more parameters (e.g., temporal and spatial thresholds, filter parameters and the like) as well as to select one or more SOI that can be stored in memory for further processing and analysis. The output system 162 thus can generate corresponding output data 174 that can in turn be rendered by the visualization engine 184 as a corresponding graphical output in a display 192, such as including an electrocardiographic map 194. For example, the map generator can generate maps and other output visualizations, such as can include a plurality of signal waveforms and associated metadata based on the data 159, the data 170 or based on a combination of the invasive and non-invasive data.

Additionally, in some examples, the output data 174 can be utilized by the system 158 in connection with controlling delivery of therapy. The control 160 that is implemented can be fully automated control, semi-automated control (partially automated and responsive to a user input) or manual control based on the output data 174. In some examples, the control 160 of the therapy system can utilize the output data to control one or more therapy parameters. As an example, the control 160 can control delivery of ablation therapy to a site of the heart (e.g., epicardial or endocardial wall) based on one or more arrhythmia drivers identified by monitoring system 182. In other examples, an individual can view the map generated in the display to manually control the therapy system. Other types of therapy and devices can also be controlled based on the output data 174 and corresponding graphical map 194.

By way of further example, the localization engine 188 can be used to navigate the therapy delivery device 156 to a predetermined anatomical location defined by the location data for a given SOI (e.g., by SOI metadata). The control 160 can activate application of energy to the site via the device 156 in response to a user input and/or the output data 174 to deliver corresponding therapy at the site. The characterization system 182 quantifies changes between signal characteristics of the SOI and the measured real time signal. The characterization system 182 can be configured to provide the output data to include an indication of an endpoint for delivering the therapy (e.g., graphical, text and/or audible indication) based on the comparison between the signal characteristics computed (e.g., by calculator 34) based on the SOI data and based on the real time measured signals (e.g., measurement data 159 and/or 170) in response to delivering the therapy. In some cases, the endpoint can be determined by quantifying of changes between signal characteristics for a predefined SOI that is substantially the same location where the therapy is applied. In other examples, the endpoint can be determined by monitoring signal characteristics at one or more spatial locations that are spaced apart from target delivery site.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A method comprising:
   receiving electrophysiological monitoring data representing one or more substantially real time electrical signals based on measurements from one or more respective electrodes;
   selecting at least one subset time interval of the electrophysiological monitoring data as a signal of interest (SOI) either in response to a SOI selection user input entered via a user input device, or based on user-programmed selection data defining one or more anatomical landmarks or predefined anatomical regions;
   storing in memory SOI data corresponding to each selected SOI, the SOI data including location data identifying a respective spatial location for each selected SOI in relation to anatomical geometry and that programmatically links each selected SOI to a respective anatomical location;
   based on the stored SOI data including the location data, quantifying changes between signal characteristics of real time signals acquired during or in response to delivery of a therapy to a patient for one or more respective anatomical locations and the at least one SOI that is associated with each of the respective anatomical locations; and generating an output based on the quantifying to characterize spatially local signal changes with respect to each of the respective anatomical locations, the output providing an indication of parameters and/or endpoint for delivery of the therapy to the patient based on the spatially local signal changes.

2. The method of claim 1, wherein the SOI data for each SOI further comprises:
time data identifying a corresponding time interval; and
values of one or more signal characteristics computed for the respective SOI.

3. The method of claim 1, further comprising:
navigating a therapy delivery device to a target anatomical location defined by the location data for a given SOI; and
delivering a therapy at the target anatomical location, corresponding to the given SOI, based on the quantified changes between the real time signals for the target anatomical location and the given SOI associated with the target anatomical location.

4. The method of claim 3, wherein the quantifying changes is computed over a given time interval from the SOI data for at least one other anatomical location and in response to delivering the therapy at the target anatomical location.

5. The method of claim 1, further comprising:
navigating a therapy delivery device to a target anatomical location defined by the location data for a given SOI; and
delivering a therapy at the target anatomical location based on the quantifying of changes for the signal characteristics of at least one other anatomical location that is spaced apart from the target anatomical location associated with the given SOI.

6. The method of claim 5, wherein the output provides the indication of the endpoint for the delivery of the therapy, which endpoint is based on the quantifying of the changes computed over a given time interval from the SOI data for the at least one other anatomical location and in response to delivering the therapy at the target anatomical location.

7. The method of claim 1, further comprising:
analyzing the SOI data for a plurality of anatomical locations in a region of the patient's heart to compute a score for each of the SOIs; and
ranking each of the SOIs based on its associated score to classify a subset of the SOIs within the region as high priority SOIs and to classify at least another subset of the plurality of anatomical locations in the region as low priority SOIs.

8. The method of claim 7, wherein generating the output further comprises generating a graphical map of the region that differentiates between the high priority SOIs and the low priority SOIs.

9. The method of claim 7, further comprising computing the values of the one or more signal characteristics to include at least two of the group consisting essentially of a cycle length, an indication of disorganization, an indication of fractionation and a percentage of activation for each SOI and each of the one or more real time signals.

10. The method of claim 7, wherein the score comprises a weighted score that is computed for each of the SOIs based on the values of the one or more signal characteristics.

11. The method of claim 1, wherein generating the output further comprises providing an indication of the values computed for the at least one SOI displayed in a portion of a visualization space adjacent a visualization of the respective SOI and a visualization of the one or more real time signals.

12. The method of claim 1, wherein the monitoring data from which the at least one SOI is selected comprises electrical signals obtained from a set of non-invasive electrodes positioned outside of the patient's body, and
wherein another part of the monitoring data, corresponding to the real time signals acquired for the one or more respective anatomical locations, comprises electrical signals measured from at least one electrode positioned invasively within the patient's body.

13. The method of claim 1, wherein the monitoring data comprises data obtained from a common set of electrodes positioned either inside or outside of the patient's body.

14. The method of claim 1, wherein the selecting the at least one SOI comprises selecting the at least one SOI in response to the SOI selection user input entered via a user input device.

15. The method of claim 2, wherein the SOI data for each SOI further comprises metadata, the metadata comprising data identifying at least one time segment of the SOI programmatically linked to a respective predefined anatomic location,
wherein each respective predefined anatomic location is programmable in response to user input or is set based on a user profile specifying the respective predefined anatomical location.

16. A system, comprising:
non-transitory memory configured to store executable instructions and data, the data including electrophysiological monitoring data representing one or more substantially real time electrical signals based on measurements from one or more respective electrodes;
a processor configured to access the memory and execute the instructions, the instructions comprising:
selecting at least one subset time interval of the electrophysiological monitoring data as a signal of interest (SOI) either in response to a SOI selection user input entered via a user input device, or based on user-programmed selection data defining one or more anatomical landmarks or predefined anatomical regions, to store SOI data in the memory for each selected SOI, the SOI data including location data identifying a respective spatial location for each selected SOI in relation to anatomical geometry and that programmatically links each selected SOI to a respective anatomical location;
computing signal characteristics for each of the SOIs based on the stored SOI data including the location data and for real time signals acquired during or in response to delivery of a therapy to a patient for one or more respective anatomical locations;
providing analysis data that quantifies changes in the computed signal characteristics; and
generating an output based on the quantifying to provide an indication of parameters and/or endpoint for delivery of the therapy to the patient based on the analysis data quantifying changes in the computed signal characteristics.

17. The system of claim 16, wherein the computing signal characteristics comprises:
computing values of one or more signal characteristics for each the SOIs based on the stored SOI data and for each of the one or more real time signals based on the monitoring data, the signal characteristics including at least one of a cycle length, an indication of disorganization, an indication of fractionation and a percentage of activation for each SOI; and comparing the computed values for SOIs relative to computed values for corresponding real time signals to provide the analysis data.

18. The system of claim 17, wherein the computing signal characteristics comprises:

analyzing the SOI data for a plurality of anatomical locations in a region of the patient's heart to compute an associated score which is stored as part of the SOI data for each of the SOIs, and ranking each of the SOIs based on its associated score to classify a first subset of the SOIs within the region as high priority SOIs and to classify another subset of the respective anatomical locations as lower priority SOIs.

19. The system of claim 16, further comprising a therapy delivery system configured to deliver therapy to at least one target site, wherein the computing signal characteristics comprises analyzing the SOI data to identify at least one anatomical location to define each target site.

20. The system of claim 19, wherein the generating the output generates the output to include an indication of an endpoint for delivering the therapy at the target site, corresponding to a given SOI, based on the quantified changes in the computed signal characteristics.

21. The system of claim 20, wherein the computing signal characteristics determines the endpoint for delivering the therapy at the target site based on at least one of (i) quantifying changes in signal characteristics for between the real time signals for the target site and the given SOI associated with the target site or (ii) quantifying changes in signal characteristics for at least one other anatomical location that is spaced apart from the target site.

22. The system of claim 19, wherein the instructions further comprise determining spatial coordinates for the at least one target site based on SOI data, the therapy delivery system employing the spatial coordinates to navigate a therapy delivery device of the therapy delivery system to the spatial coordinates of the target site.

23. The system of claim 19, further comprising a measurement system configured to receive and process electrical signals sensed by at least one electrode.

24. The system of claim 23, wherein the measurement system comprises a non-invasive measurement system configured to receive input electrical signals from an arrangement of sensors distributed outside of a patient's body, the instructions further comprising computing the substantially real time electrical signals for a region within the patient's body based on the input electrical signals to provide at least a portion of the monitoring data as reconstructed electrograms.

25. The system of claim 24, wherein the measurement system further comprises an invasive measurement system configured to receive invasively measured electrical signals from at least one sensor within the patient's body to provide the substantially real time electrical signals for the region within the patient's body corresponding to at least another portion of the monitoring data.

* * * * *